(12) United States Patent
Holm et al.

(10) Patent No.: US 10,058,442 B2
(45) Date of Patent: Aug. 28, 2018

(54) ENDOPROSTHESIS DELIVERY SYSTEM

(75) Inventors: Brian C. Holm, Mountain View, CA (US); Shane P. Rogers, San Jose, CA (US); Aniceto Trujillo, Sunnyvale, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/439,773

(22) Filed: Apr. 4, 2012

(65) Prior Publication Data

US 2012/0316637 A1 Dec. 13, 2012

Related U.S. Application Data

(60) Provisional application No. 61/473,503, filed on Apr. 8, 2011.

(51) Int. Cl.
*A61F 2/06* (2013.01)
*A61F 2/966* (2013.01)

(52) U.S. Cl.
CPC ...... *A61F 2/966* (2013.01); *A61F 2002/9665* (2013.01)

(58) Field of Classification Search
CPC .......... A61F 2002/962; A61F 2002/966; A61F 2002/9665; A61F 2/962; A61F 2/966
USPC .................................. 623/1.11, 1.12
See application file for complete search history.

(56) References Cited

U.S. PATENT DOCUMENTS

| 5,647,857 | A | | 7/1997 | Anderson et al. | |
|---|---|---|---|---|---|
| 5,735,859 | A | * | 4/1998 | Fischell | A61F 2/95 606/108 |
| 5,824,041 | A | * | 10/1998 | Lenker | A61F 2/07 606/195 |
| 6,447,540 | B1 | | 9/2002 | Fontaine et al. | |
| 8,025,692 | B2 | * | 9/2011 | Feeser | 623/1.12 |
| 8,066,756 | B2 | * | 11/2011 | Rasmussen et al. | 623/1.12 |
| 2004/0122503 | A1 | | 6/2004 | Campbell et al. | |
| 2005/0154443 | A1 | * | 7/2005 | Linder et al. | 623/1.11 |
| 2006/0247757 | A1 | * | 11/2006 | Kaufmann et al. | 623/1.12 |
| 2006/0259124 | A1 | * | 11/2006 | Matsuoka | A61F 2/966 623/1.12 |
| 2007/0260302 | A1 | | 11/2007 | Igaki | |
| 2008/0319524 | A1 | | 12/2008 | Yachia et al. | |
| 2009/0259298 | A1 | * | 10/2009 | Mayberry | A61F 2/07 623/1.35 |
| 2011/0034987 | A1 | | 2/2011 | Kennedy | |

FOREIGN PATENT DOCUMENTS

| EP | 1982677 | 10/2008 |
|---|---|---|
| WO | 98/20812 | 5/1998 |
| WO | 2007/021708 | 2/2007 |

* cited by examiner

*Primary Examiner* — Gregory Anderson
*Assistant Examiner* — Sarah Simpson

(57) ABSTRACT

The present disclosure relates to catheters for delivering medical devices to a human patient's vasculature. A catheter comprises a sock which covers the medical device at the end of the catheter, and an introducer sheath which is reduced in diameter. This reduced diameter introducer sheath minimizes the crossing of the catheter.

21 Claims, 4 Drawing Sheets

ENDOPROSTHESIS DELIVERY SYSTEM

CROSS REFERENCE TO RELATED APPLICATIONS

This application claims priority to U.S. Provisional Application No. 61/473,503, entitled "ENDOPROSTHESIS DELIVERY SYSTEM" filed Apr. 8, 2011, which is hereby incorporated by reference in its entirety.

FIELD

The present disclosure relates generally to catheters, and more specifically, to a system for delivering an endoprosthesis to a treatment region in the vasculature of a patient.

BACKGROUND

Current methods for providing medical treatment to human vasculature involve the use of catheters. In many cases, catheters are used to deliver endoprostheses, such as, for example, stents and stent grafts (self-expanding or otherwise), bifurcated stents and stent grafts, drug-eluting stents, and vascular filters, such as inferior vena cava filters, as well as endoluminal imaging devices.

Frequently catheters enter the body through an orifice or incision. Catheters are typically inserted through main arteries, such as the femoral or brachial artery, and then navigated through the vasculature to the region requiring treatment. Once the tip of the catheter is in the treatment region, it may deploy a medical device. In many cases, the device is a self-expanding endoprosthesis. In other configurations, a balloon may be used to expand the endoprosthesis to its operational size.

One significant problem with current endoprosthesis delivery systems is the size of the incision required to accommodate the system. This incision may be referred to as the crossing of the catheter. Large crossings may cause increased patient discomfort, longer recovery times, and potential scarring. Thus, a need exists for endoprosthesis delivery systems that can safely and effectively deliver endoprostheses to the treatment region within the vasculature through a relatively small crossing. Those skilled in the art will recognize numerous advantages of such embodiments over the prior art, for example, reducing the size of the crossing necessary to deliver endoprostheses.

SUMMARY

An endoprosthesis delivery device of the present disclosure comprises a catheter, which further comprises an endoprosthesis, a catheter shaft, an introducer sheath, a sock, and a sock securing element. The introducer sheath has an outer diameter equal to or less than the outer diameter of the endoprosthesis in a compressed and/or collapsed configuration. The sock extends from the trailing end of the introducer sheath to the leading end, exits the introducer sheath, and continues over the endoprosthesis.

Another endoprosthesis delivery device of the present disclosure comprises a catheter having a trailing and leading end, a stent located at the leading end of the catheter, an introducer sheath, a leading tip, a sock, a sock retaining segment, a sock securing suture, and a sock removal mechanism located at the trailing end of the catheter. The introducer sheath has an outer diameter less than or equal to the outer diameter of the stent in its collapsed and/or compressed configuration. The sock extends from the sock removal mechanism, through the introducer sheath and beyond its leading end, continuing over the stent and sock retaining segment. The sock retaining segment and sock securing suture work together to maintain the position of the sock along the catheter before the stent is delivered to the treatment area.

A method of delivering an endoprosthesis to a treatment region within a human patient comprises inserting an endoprosthesis delivery system into the body of the patient, the endoprosthesis delivery system comprising an endoprosthesis, a catheter shaft, an introducer sheath having an inner diameter equal to or less than the endoprosthesis, a sock extending from the leading end of the introducer sheath over the endoprosthesis and a sock positioning element, guiding the leading end of the catheter shaft to the region to be treated, retracting the sock, deploying the endoprosthesis, and retracting the catheter shaft from the body.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION

Figure 1:
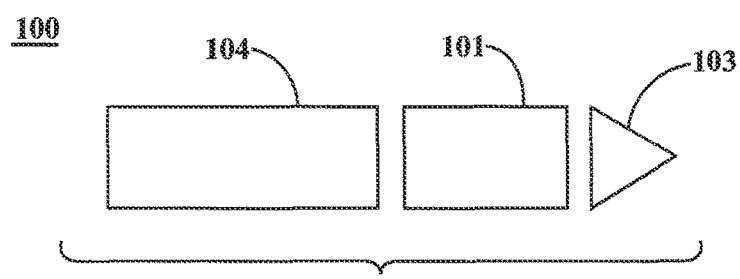
FIG. 1 illustrates a side view of a catheter in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

An endoprosthesis delivery system of the present disclosure comprises a catheter shaft, introducer sheath, endoprosthesis, and sock. In such an embodiment, the catheter shaft is housed within the introducer sheath, and the endoprosthesis is situated at the leading end of the catheter shaft, outside of the introducer sheath. The sock, which surrounds the catheter shaft within the introducer sheath, exits the leading end of the introducer sheath and covers the endoprosthesis. In various embodiments, the outer diameter of the introducer sheath is less than or equal to the outer diameter of the endoprosthesis in its collapsed and/or compressed configuration.

In the present disclosure, the term "leading" is used to describe a position inside the body of a patient that is farthest from the entry point of the device into the body. For example, the leading end of a catheter refers to the end, inside the vasculature of the body, which is farthest from the entry point of the catheter. The term "trailing" is used to describe a position closest to the entry point of a device into the body of a patient. For example, the trailing end of a catheter refers to the portion of the catheter outside of the body of a patient.

Turning now to such embodiments, and with reference to FIG. 1, catheter 100 is an endoprosthesis delivery system. Catheter 100 includes an introducer sheath 104, an endoprosthesis 101 and a leading tip 103. In various embodiments, endoprosthesis 101 is positioned between introducer sheath 104 and leading tip 103. In various embodiments, endoprosthesis 101 can be an expandable stent or stent graft. In an aspect of these embodiments, endoprosthesis 101 is a self-expanding stent or stent graft. In various embodiments, before catheter 100 is inserted into the body of a patient, endoprosthesis 101 is in a collapsed and/or compressed state.

In various embodiments, the inner diameter of introducer sheath 104 is less than or equal to the outer diameter of endoprosthesis 101 in a collapsed and/or compressed state. In these embodiments, because the outer diameter of endoprosthesis 101 is larger than the inner diameter of introducer sheath 104, endoprosthesis 101 cannot be deployed from within introducer sheath 104. In an aspect of these embodiments, the outer diameter of introducer sheath 104 may also be less than or equal to the outer diameter of endoprosthesis 101 in a collapsed and/or compressed state. In embodiments in which the outer diameter of introducer sheath 104 is equal to the outer diameter of endoprosthesis 101, introducer sheath 104 and endoprosthesis 101 form an integrated tube of constant diameter from the entry point of introducer sheath 104 to the leading end of endoprosthesis 101.

Figure 2A:
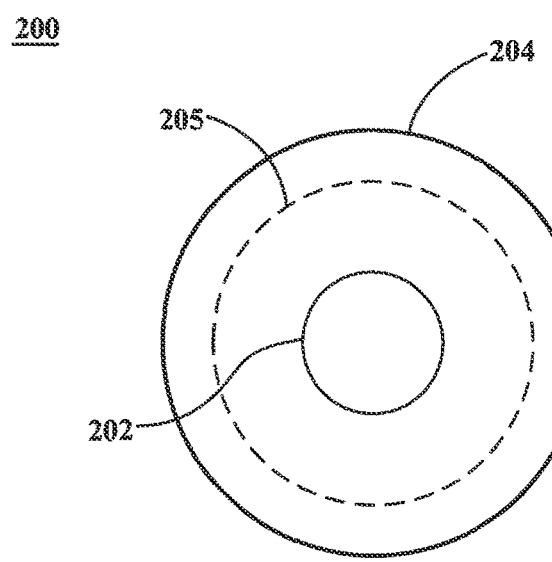
FIGS. 2A and 2B illustrate axial cross sectional views of a catheter in accordance with the present disclosure.

With reference to FIG. 2A, catheter 200 is an endoprosthesis delivery device. In various embodiments, catheter 200 comprises a catheter shaft 202, introducer sheath 204 and sock 205. In these embodiments, introducer sheath 204 is inserted into the vasculature. Catheter shaft 202 and sock 205 pass through introducer sheath 204 and are navigated towards the treatment area in the vasculature.

Figure 2B:
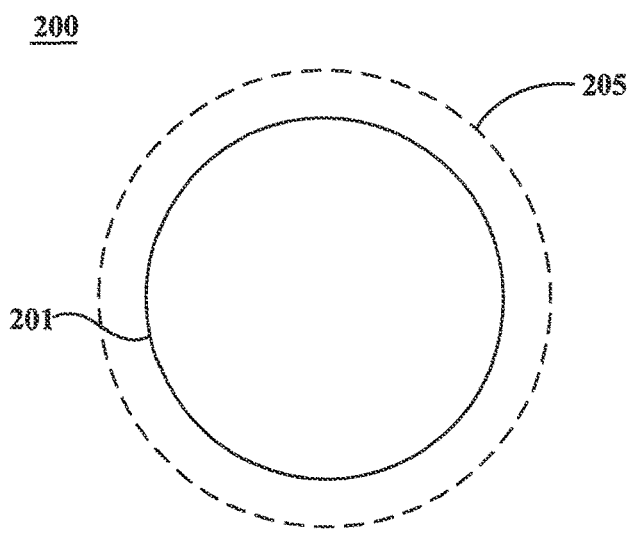

With reference to FIG. 2B, catheter 200 further comprises an endoprosthesis 201. In various embodiments, endoprosthesis 201 is situated at the leading end of catheter shaft 202. Endoprosthesis 201 may comprise, for example, a stent. In an aspect of these embodiments, endoprosthesis comprises a self-expanding stent or stent graft in a compressed and/or collapsed configuration. However, any endoprosthesis which may be delivered by a catheter to a treatment region is within the scope of the present disclosure.

In various embodiments, catheter 200 further comprises a sock 205. In these configurations, sock 205 has an inner diameter greater than or equal to that of catheter shaft 202 and less than the inner diameter of introducer sheath 204. Sock 205 surrounds catheter shaft 202, passes through introducer sheath 204, and extends outward from the leading end of introducer sheath 204. Sock 205 then surrounds the exterior of endoprosthesis 201. In various embodiments, sock 205 has an inner diameter greater than or equal to that of endoprosthesis 201 and greater than or equal to that of introducer sheath 204.

In various embodiments, sock 205 protects endoprosthesis 201 as the device is delivered to the treatment region. For example, sock 205 may prevent endoprosthesis 201 from becoming contaminated as the catheter 200 is navigated to the treatment region. In various embodiments, sock 205 covers both endoprosthesis 201 and a deployment sheath (not shown). In these configurations, the deployment sheath surrounds endoprosthesis 201 and retains it in a collapsed and/or compressed configuration. In embodiments which do not utilize a deployment sheath, sock 205 may provide both protection against contamination and retention of endoprosthesis 201 in a collapsed and/or compressed configuration.

Sock 205 may comprise, for example, a biologically compatible material, such as a polymer. In an aspect of these embodiments, sock 205 comprises ePTFE. However, any material which allows sock 205 and endoprosthesis 201 to traverse a vasculature without causing adverse biological impact is within the scope of the present disclosure, such as, for example, nylons, polycarbonates, polyethylenes, polypropylenes, polytetrafluoroethylenes, polyvinyl chlorides, polyurethanes, polysiloxanes, and other biocompatible materials.

In various embodiments, the inner diameter of introducer sheath 204 is less than or equal to the outer diameter of endoprosthesis 201 in a collapsed and/or compressed state. In an aspect of these embodiments, the outer diameter of introducer sheath 204 is less than or equal to the outer diameter of endoprosthesis 201.

In various embodiments, catheter shaft 202 of catheter 200 comprises a guidewire. However, any flexible shaft which provides support for catheter 200 is within the scope of the present disclosure. The term "flexible shaft" includes any longitudinally extending structure with or without a lumen therethrough. Thus, flexible shafts include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Flexible shafts can be of any material and can have any cross-sectional shape including but not limited to profiles that are circular, oval, triangular, square, polygon shaped or randomly shaped.

Because introducer sheath 204 provides the medical device being delivered access to the vasculature, it is important that introducer sheath 204 comprise a material that is biologically compatible material. In various embodiments, introducer sheath 204 comprises a polymer, such as, for example, Pebax. However, any material which allows introducer sheath to traverse a vasculature without causing adverse biological impact is within the scope of the present disclosure, such as, for example, ePTFE, nylons, polycarbonates, polyethylenes, polypropylenes, polytetrafluoroethylenes, polyvinyl chlorides, polyurethanes, polysiloxanes, and other biocompatible materials.

Figure 3A:
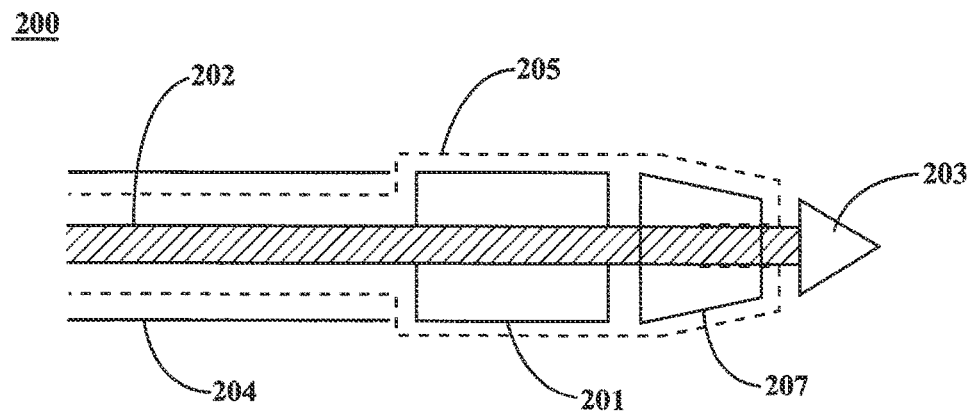
FIGS. 3A, 3B, and 3C illustrate longitudinal cross-sectional views of catheters in accordance with the present disclosure.
Figure 3B:
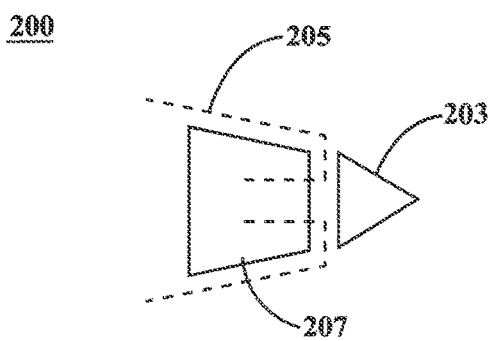

With reference to FIGS. 3A and 3B, catheter 200 is the endoprosthesis delivery system of FIGS. 2A and 2B. In various embodiments, catheter 200 further comprises a leading tip 203. Leading tip 203 may be connected to the leading end of catheter shaft 202. In various embodiments, leading tip 203 comprises a tip capable of piercing a thrombus. In various embodiments, leading tip 203 may comprise a material that is radiopaque and/or comprises a marker. Leading tip 203 can comprise, for example, a biologically compatible material, such as a polymer. However, any material which allows leading tip to navigate a vasculature without causing adverse biological impact is within the scope of the present disclosure.

In various embodiments, endoprosthesis 201 is positioned between the leading end of introducer sheath 204 and leading tip 203. This configuration allows leading tip 203 to remove or traverse potential blockages or thrombus in the vasculature and provides access to the treatment area by endoprosthesis 201.

Figure 3C:
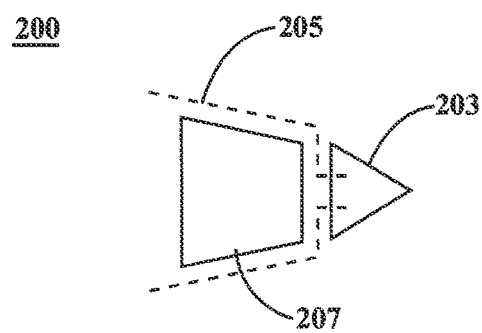

With initial reference to FIG. 3C, catheter 200 comprises a leading tip 203. In various embodiments, leading tip 203 comprises a cavity. In an aspect of these embodiments, the leading end of sock 205 enters and is retained within a conically-shaped cavity of leading tip 203.

Catheter 200 further comprises a sock retaining segment 207. In various embodiments, sock retaining segment 207 is positioned between endoprosthesis 201 and leading tip 203. Sock retaining segment 207 can, for example, include a cavity into which the leading end of sock 205 enters. In these embodiments, sock retaining segment 207 may retain the position of sock 205 by preventing sock 205 from changing position as catheter 200 traverses the vasculature.

In various embodiments, sock 205 extends from the leading end of the introducer sheath 204, over endoprosthesis 201, over sock retaining segment 207, and finally enters the cavity of sock retaining segment 207 and/or leading tip 203. Leading tip 203 can, for example, include an indented lip, which allows sock retaining segment 207 to interface with leading tip 203 and creates a smooth transition between the end of the sock 205 and the surface of leading tip 203.

Figure 4:
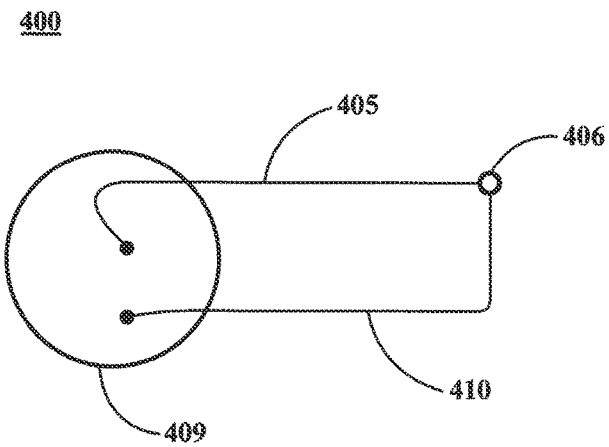
FIG. 4 illustrates a cross sectional view of a segment of a catheter in accordance with the present disclosure.

With reference to FIG. 4, catheter 400 is an endoprosthesis delivery system. Various embodiments of catheter 400 comprise a sock 405 and sock securing element 406. Sock securing element 406 can comprise, for example, a suture which reduces the diameter of sock 405 at or near its leading end over the reduced diameter, or within the cavity, of sock retaining segment 207. This prevents sock 405 from moving from the desired position as the device is inserted into the patient and navigated through the vasculature.

In various embodiments, catheter 400 further comprises a pull string 410. Pull string 410 may be attached to sock securing element 406. In various embodiments, pull string 410 may be actuated by, for example, providing tension to pull string 410. In these embodiments, when pull string 410 is actuated, sock securing element 406 releases from sock 405. In an aspect of these embodiments, sock securing element 406 can comprise a suture that releases and restores sock 405 to its initial inner diameter. This allows sock 405 to be removed from catheter 400.

In various embodiments, catheter 400 further comprises a sock removal mechanism 409. In these embodiments, sock removal mechanism 409 may be connected to sock 405. When sock removal mechanism 409 is actuated, sock 405 is removed from catheter 400. Sock 405 can extend from the inside of an introducer sheath (not shown) to cover an endoprosthesis (not shown). As sock 405 is removed, the endoprosthesis becomes exposed and may be deployed in the treatment area.

In various embodiments, sock removal mechanism 409 is connected to both sock 405 and pull string 410. In these embodiments, pull string 410 further comprises a section of additional length, such that pull string 410 is not in tension. Sock 405 also further comprises a section of additional length. The section of additional length of pull string 410, can, for example, be shorter than the section of additional length of sock 405. In these configurations, when tension is applied to sock removal mechanism 409, pull string 410 becomes taught before sock 405. This allows for pull string 410 to release sock securing element 406, which expands the diameter of sock 405, and allows sock 405 to then be removed from the body.

In an embodiment, the endoprosthesis is a self-expanding stent or stent graft, and actuation of sock removal mechanism 409 allows the endoprosthesis to expand and deploy to the treatment area. In other embodiments, the actuation of sock removal mechanism 409 allows for final placement of the endoprosthesis in the vasculature, and other means may be used, such as, for example, an expanding balloon, to deploy the endoprosthesis.

Figure 6:
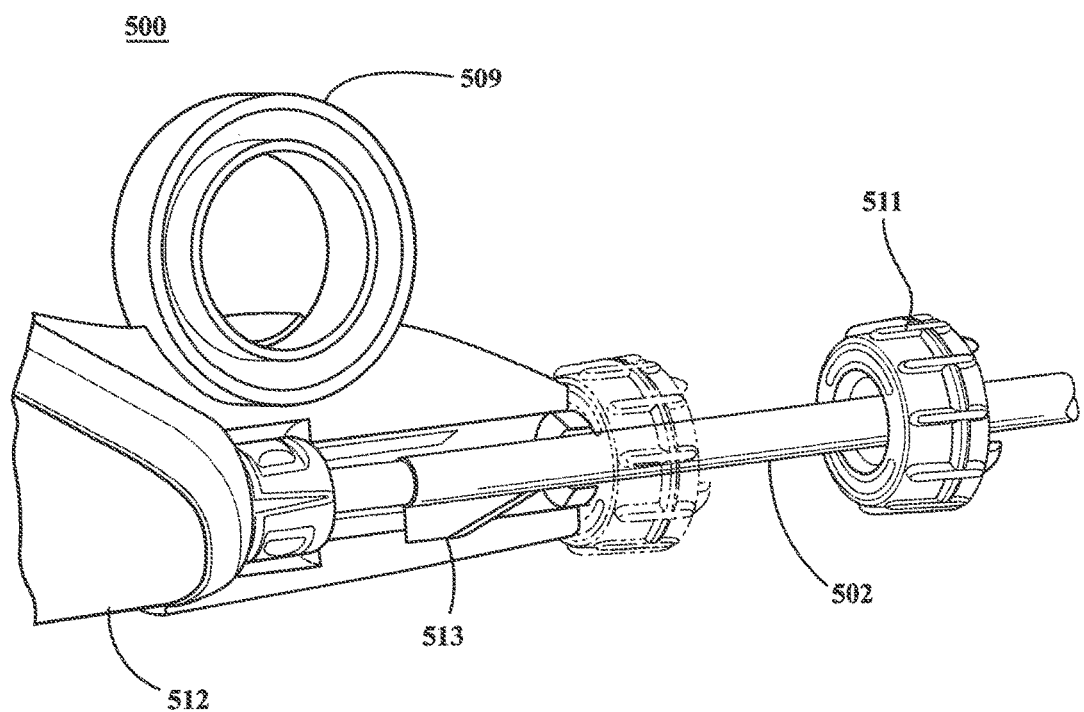
FIG. 6 illustrates a cross section of a catheter in accordance with the present disclosure.
Figure 5:
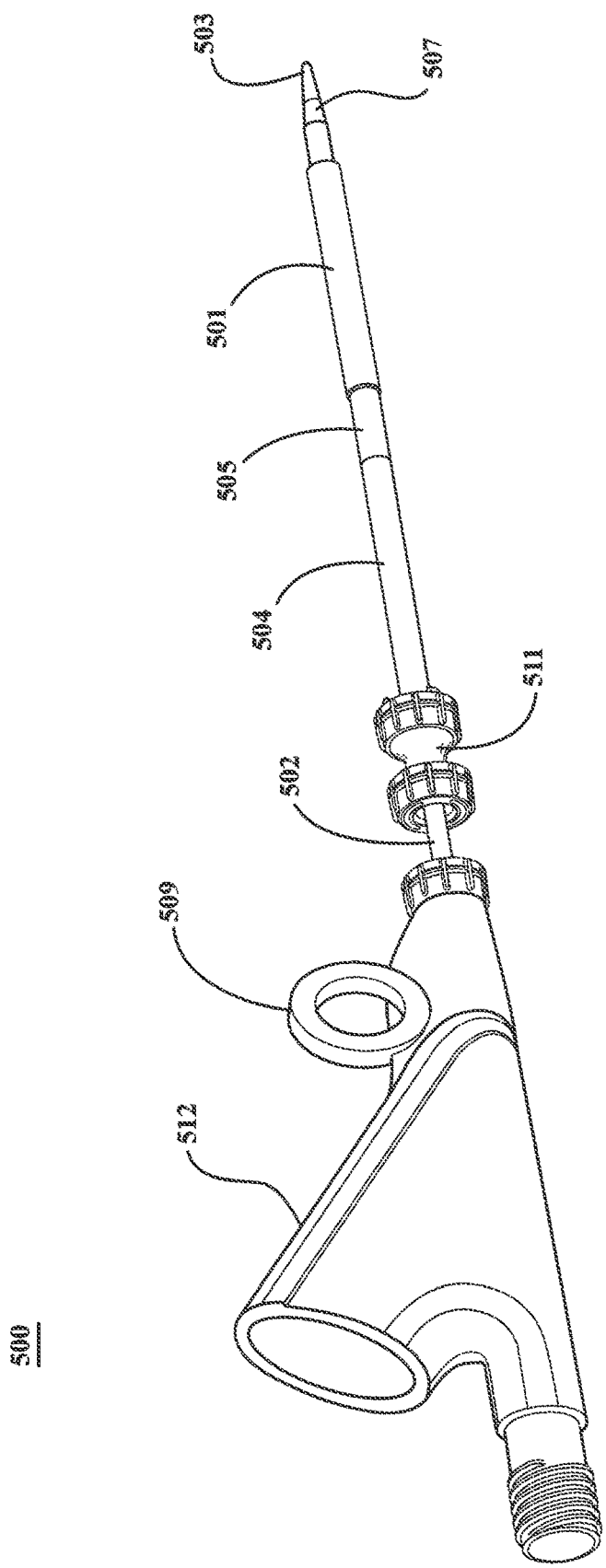
FIG. 5 illustrates a side view of a catheter in accordance with the present disclosure.

With reference now to FIGS. 5 and 6, catheter 500 is an endoprosthesis delivery device. Catheter 500 comprises a handle 512, through which catheter shaft 502 is controlled. Catheter shaft 502 passes through a valve 511 and into introducer sheath 504. Sock 505 passes through introducer sheath 504 and surrounds catheter shaft 502. Sock 505 exits the introducer sheath 504 at its leading end.

Endoprosthesis 501 is positioned on catheter shaft 502 at the leading end of the introducer sheath 504 prior to insertion of catheter 500 into the body. Though not shown in the drawing, sock 505, after exiting introducer sheath 504, surrounds endoprosthesis 501. A sock retaining segment 507 is positioned adjacent to endoprosthesis 501. At the leading end of catheter shaft 502, and adjacent to sock retaining segment 507, is a leading tip 503. A sock removal mechanism 509 is connected to sock 505 and situated on handle 512.

With initial reference to FIG. 6, a cross sectional view of catheter 500 is presented. Catheter 500 comprises a slitting blade 513. In various embodiments, when sock removal mechanism 509 is actuated, slitting blade 513 cuts sock 505, which allows it to be removed from catheter shaft 502. In other embodiments, sock 205 can be configured so that it can be removed without the use of slitting blade 513, such as, for example, by using a perforated film, a longitudinally-oriented film, and/or a film of varying thickness, such that sock 205 can be relatively easily torn or deconstructed at a particular location. However, any means of facilitating the removal of sock 505 from catheter shaft 502 is within the scope of the present disclosure.

Thus, the endoprosthesis delivery system of the present disclosure provides an effective, low crossing system capable of delivering endoprostheses to a vasculature.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthesis delivery system comprising:
   an endoprosthesis;
   a catheter shaft having a leading tip;

an introducer sheath having a leading end and an inner diameter less than the outer diameter of the endoprosthesis;
a sock extending from the leading end of the introducer sheath over the endoprosthesis, the sock providing an initial diameter;
a tapered sock retaining segment, wherein the sock extends over the tapered sock retaining segment and into a cavity between the leading tip and the sock retaining segment, the sock being retained in the cavity so as to prevent displacement of the sock as the catheter traverses vasculature during delivery of the endoprosthesis to a treatment site, the cavity being formed along a leading surface of the sock retaining segment which is spaced apart from and faces the leading tip; and
a sock securing element comprising a suture configured to constrain the sock distal to the endoprosthesis to reduce the initial diameter of the sock to a reduced diameter distal to the endoprosthesis, the sock securing element further configured to release the sock in response to actuation of a pull string to restore the reduced diameter to the initial diameter and allow a distal end of the sock in the initial diameter to be retracted over the endoprosthesis.

2. The system of claim 1 further comprising a sock removal mechanism.

3. The system of claim 2 wherein the sock removal mechanism further comprises a blade.

4. The system of claim 3 wherein the sock removal mechanism further comprises a deployment ring.

5. The system of claim 1, wherein the catheter shaft comprises a guidewire lumen.

6. The system of claim 1, wherein the endoprosthesis comprises a stent.

7. The system of claim 6, wherein the endoprosthesis comprises a self-expanding stent.

8. The system of claim 1,
wherein the tapered sock retaining segment comprises the cavity, and
wherein a leading end of the sock is within the cavity.

9. The system of claim 1, wherein the leading tip comprises the cavity.

10. The system of claim 1, wherein the leading tip comprises an indented lip, which allows the sock retaining segment to interface with the leading tip to provide a smooth transition between an end of the sock and an exterior surface of the leading tip.

11. The system of claim 1, further comprising a deployment sheath surrounding the endoprosthesis and retaining it in a collapsed configuration, wherein the sock extends outward from the leading end of introducer sheath and surrounding the endoprosthesis and the deployment sheath.

12. The system of claim 1, wherein the sock comprises ePTFE.

13. The system of claim 1, wherein the sock is of tubular construction.

14. The system of claim 1, further comprising a deployment sheath surrounding the endoprosthesis and retaining it in a collapsed configuration,
wherein the sock extends outward from the leading end of introducer sheath and surrounding the endoprosthesis and the deployment sheath, and
wherein the endoprosthesis comprises a self-expanding stent.

15. An endoprosthesis delivery system comprising:
an endoprosthesis;
a catheter shaft having a leading tip;
an introducer sheath having a leading end and an inner diameter less than the outer diameter of the endoprosthesis;
a sock extending from the leading end of the introducer sheath over the endoprosthesis, the sock providing an initial diameter; and
a sock securing element comprising a suture configured to constrain the sock distal to the endoprosthesis to reduce the initial diameter of the sock to a reduced diameter distal to the endoprosthesis,
wherein the sock securing element retains the sock so as to prevent displacement of the sock as the catheter traverses vasculature during delivery of the endoprosthesis to a treatment site until the sock securing element is actuated to expand the reduced diameter of the sock to the initial diameter and allow a distal end of the sock in the initial diameter to be retracted over the endoprosthesis to allow deployment of the endoprosthesis.

16. The system of claim 15, wherein the sock is of tubular construction.

17. The system of claim 15, further comprising a deployment sheath surrounding the endoprosthesis and retaining it in a collapsed configuration, wherein the sock extends outward from the leading end of introducer sheath and surrounding the endoprosthesis and the deployment sheath.

18. The system of claim 15, wherein the endoprosthesis comprises a stent.

19. The system of claim 15, wherein the sock comprises ePTFE.

20. An endoprosthesis delivery system comprising:
an endoprosthesis;
a catheter shaft having a leading tip;
an introducer sheath having a leading end and an inner diameter less than the outer diameter of the endoprosthesis;
a deployment sheath surrounding the endoprosthesis and retaining it in a collapsed configuration;
a sock of tubular construction extending outward from the leading end of introducer sheath and surrounding the endoprosthesis and the deployment sheath, the sock providing an initial diameter;
a tapered sock retaining segment, wherein the sock extends over the tapered sock retaining segment and into a cavity between the leading tip and the sock retaining segment, the sock being retained in the cavity so as to prevent displacement of the sock as the catheter traverses vasculature during delivery of the endoprosthesis to a treatment site, the cavity being formed along a leading surface of the sock retaining segment which is spaced apart from and faces the leading tip; and
a sock securing element comprising a suture configured to constrain the sock distal to the endoprosthesis to reduce the initial diameter of the sock to a reduced diameter distal to the endoprosthesis,
wherein the sock securing element retains the sock so as to prevent displacement of the sock as the catheter traverses vasculature during delivery of the endoprosthesis to a treatment site until the sock securing element is actuated to expand the reduced diameter of the sock to the initial diameter and allow a distal end of the sock in the initial diameter to be retracted over the endoprosthesis to allow deployment of the endoprosthesis.

21. The system of claim 20, wherein the sock comprises ePTFE.

* * * * *